United States Patent [19]

Watanabe

[11] Patent Number: 4,973,681

[45] Date of Patent: Nov. 27, 1990

[54] PROCESS FOR STABILIZING POLYOL FATTY ACID POLYESTERS

[75] Inventor: Mutsuhito Watanabe, Tokyo, Japan

[73] Assignees: Showa Sangyo Co., Ltd.; Mitsubishi Chemical Industries Ltd., both of Tokyo, Japan

[21] Appl. No.: 415,732

[22] Filed: Oct. 2, 1989

[30] Foreign Application Priority Data

Oct. 5, 1988 [JP] Japan ................... 63-249728

[51] Int. Cl.$^5$ .................. C07H 13/00; C07H 1/00; C08B 37/00
[52] U.S. Cl. .................... 536/119; 536/115; 536/116; 536/124; 536/18.5
[58] Field of Search ............... 536/119, 115, 116, 124, 536/18.5; 514/23, 558; 562/580, 582, 584, 585

[56] References Cited

U.S. PATENT DOCUMENTS

| | | | |
|---|---|---|---|
| 3,872,020 | 3/1975 | Yamagishi et al. | 536/119 |
| 4,034,083 | 7/1977 | Mattson | 514/53 |
| 4,678,672 | 7/1987 | Dartey et al. | 426/19 |

FOREIGN PATENT DOCUMENTS

| | | |
|---|---|---|
| 204494 | 12/1986 | European Pat. Off. . |
| 61-15046 | 4/1986 | Japan . |
| 62-129242 | 6/1987 | Japan . |
| 62-215598 | 9/1987 | Japan . |

*Primary Examiner*—Ronald W. Griffin
*Assistant Examiner*—Everett White
*Attorney, Agent, or Firm*—Armstrong, Nikaido, Marmelstein, Kubovcik & Murray

[57] ABSTRACT

A polyol fatty acid polyester is stabilized by a polybasic oxy acid for using the polyester in safety, in a field of foods.

7 Claims, No Drawings

PROCESS FOR STABILIZING POLYOL FATTY ACID POLYESTERS

BACKGROUND OF THE INVENTION

1. Field of the Invention

The present invention relates to a process for stabilizing a polyol fatty acid polyester. The polyol fatty acid polyester stabilized by the process according to the invention may be used as an edible fat substitute having no calories.

2. Related Art

Polyol fatty acid esters have, in general, been utilized as emulsifiers, as exemplified by sucrose fatty acid esters, which have a structure, wherein the hydroxy radical(s) in a polyol, for instance saccharide or sugar alcohol and the fatty acid(s) are esterified, at an esterification degree not higher than 50%.

Recently, however, polyol fatty acid polyesters having esterification degree higher than 40% and more preferably higher than 50% have been watched with great interest, as an edible fat substitute having no calories or as a substance to be composed to an edible fat to decrease total calories of the resulting composition, since such polyol fatty acid polyesters are neither digested nor assimilated in the digestive canal and their physico-chemical properties thereof are analogous to usual edible fats. For instance, Jap. Pat. No. Sho 61-15046 (B) discloses a composition for foods, which comprises polyol fatty acid polyesters and vitamins.

The polyol fatty acid polyesters, for instance the sucrose fatty acid polyester has been prepared by, for instance, a method wherein sucrose is reacted with a fatty acid ester(s), in the presence of a solvent and an alkali catalyst [Jap. Pat. Nos. Sho 62-129242(A) and Sho 62-215598(A)].

Hitherto, it has been so considered that the polyol fatty acid polyester shows a specific or inherent stability to be estimated from its constitutional fatty acids but, in actuality, a product with constant stability has not been obtained. Although a cause generating the fluctuation in stability has not yet been elucidated, the catalyst employed for its synthesis and which possibly remains in the product, may be one of the causes.

When the polyol fatty acid polyester shall be used as the edible fat substitute and more particularly, in the field of foods, the low in stability thereof becomes a remarkable disadvantage in the view point of preservation of health.

SUMMARY OF THE INVENTION

An object of the invention is to provide a process for increasing stability of a polyol fatty acid polyester and more particularly stability to oxidation and to increase a safety in use, as one of edible fat substitutes.

The assignee company has proposed a process for treating an oil or fat with a polybasic oxy acid to remove a trace amount of metal catalyst which was employed in a hydrogenation step for refining of the oil or fat, the treatment being carried out in the purpose for restraining a natural oxidation due to air, when the oil or fat is exposed to atmosphere [Jap. Pat. No. Sho 47-87709 (A)].

The present inventor has applied the treatment using the polybasic oxy acid for the polyol fatty acid polyester to find out, unexpectedly, the fact that a remarkable improvement in stability of the polyol fatty acid polyester to oxidation can be attained, even though the object of the invention lies in stabilization thereof and thus the substance to be treated is different and the substance to be removed therefrom for stabilization thereof is also different, whereby the present invention was established.

Therefore, the invention relates to a process for stabilizing a polyol fatty acid polyester and is characterized in that the polyol fatty acid polyester is contacted with a polybasic oxy acid.

As a polyol which is one of constitutional components for the polyol fatty acid polyester to be treated by the process according to the invention, erythritol, xylitol, sorbitol, glucose, sucrose and the like may be listed, and among them, sucrose is preferable. As a fatty acid which is the other constitutional component, those having about 8 to about 22 carbon atoms, for instance caprylic acid, capric acid, lauric acid, myristic acid, myristoleic acid, palmitic acid, palmitoleic acid, stearic acid, oleic acid, elaidic acid, ricinoleic acid, linoleic acid, linolenic acid, eleostearic acid, arachinic acid, arachidic acid, behenic acid, erucic acid, docosahexaenic acid, eicosapentaenic acid and the like may be listed. The fatty acid may be in the form of a mixture. As the polybasic oxy acid to be used for the invention as a stabilizer, citric acid, malic acid, tartaric acid and the like may be listed but citric acid is preferable, in view of its availability inclusive of cost.

The main object of the invention lies in providing the safety in use of the polyol fatty acid polyester, when it shall be employed as an edible fat substitute, and thus it is preferable that hydroxy radicals in the polyol fatty acid polyester to be treated have been esterified in the level of at least 40% and more preferably higher than 50%.

When the process according to the invention is carried out, the contact between the polyol fatty acid polyester and the polybasic oxy acid may be done with use of one of various methods. For instance, the polybasic oxy acid in the solid state is added to the polyol fatty acid polyester and agitated to cause a contact therebetween, and then the polybasic oxy acid is recovered through a filtration. In another method, the polyol fatty acid polyester is passed through a filtration bed or layer containing the polybasic oxy acid under the temperature condition that the former does not cause any melt of the latter. In other method, the polybasic oxy acid or its solution is added to and mixed with the polyol fatty acid polyester. When the contacting treatment is carried out at a temperature higher than the melting point of the polybasic oxy acid, a part of the polybasic oxy acid may decompose, but no influence shall occur on the stabilizing effect, if the mixture is cooled after the treatment.

The polyol fatty acid polyester stabilized by the process according to the invention can be marketed as it is or after mixed it with another oil or fat. In the case of preparing a mixture with an oil or fat, untreated raw material of polyol fatty acid polyester may be mixed with the oil or fat (the materials are to be heated to cause a melt thereof, if it presents in solid state at room temperature) and the mixture can be treated with the polybasic oxy acid, since the resulting product shows stability the same as or substantially the same as with that prepared by mixing a previously stabilized polyol fatty acid polyester with the oil or fat.

PREFERRED EMBODIMENT OF THE INVENTION

The invention will now be explained in more detail with reference to Examples and Test Examples. Please note that the raw material of polyol fatty acid polyester employed therein was a sucrose fatty acid polyester manufactured and marketed by Mitsubishi Chemical Industries Ltd. of Tokyo, Japan (Lot No. 00612232), which has, in general, following physico-chemical properties and fatty acids composition.

| Moisture content (KF method) | 0.08% |
|---|---|
| Acid value | 0.17 |
| Melting point | 43° C. |
| Constitutional fatty acids | |
| Palmitic acid | 17.8% |
| Stearic acid | 41.4% |
| Oleic acid | 20.1% |
| Linolic acid | 13.4% |
| Linoleic acid | 1.4% |
| Other fatty acids | 5.5% |
| Esteric composition | |
| Total amount of hexa, hepta and octa esters | 100% |
| Amount of octa ester therein | 72% |

EXAMPLE 1

To sucrose fatty acid polyester heated to about 60° C. to cause a melt thereof, citric acid in the form of powder was added in 0.01% by weight and the resulting mixture was sufficiently agitated.

Then, the citric acid was recovered through a filtration to obtain a desired stabilized sucrose fatty acid polyester.

TEST EXAMPLE 1

As to the stabilized sucrose fatty acid polyester obtained in Example 1 (Test Sample A) and non-treated sucrose fatty acid polyester (Control Sample), an AOM (Active Oxygen Method) test was carried out to check a stability thereof to oxidation.

Namely, each of the samples was heated to melt the same and taken by 20 ml in a AOM test tube. The test tube was put into an oil bath maintained at 97.8° C. and clean air was blown into the tube in a rate of 2.33 ml/sec. Under such conditions, a peroxide value of the sample, increasing with time was measured from time to time.

Results are shown in following Table 1, from which it is apparent that the treatment according to the invention provides a remarkable increase in stability of the polyol fatty acid polyester.

TABLE 1

| Sample | Peroxide Value (meq./kg) | | |
|---|---|---|---|
| | After 6 hr. | After 10 hr. | After 14 hr. |
| Test A | 10.3 | 16.5 | 30.1 |
| Control | 24.9 | 37.2 | 137 |

EXAMPLE 2

Citric acid in the form of powder and diatomaceous earth were mixed in a weight ratio of 2:1 to prepare a filtering layer of 1 kg/m². While, the sucrose fatty acid polyester was heated to 80° C. and passed through the filtering layer to obtain a desired stabilized sucrose fatty acid polyester.

EXAMPLE 3

To the sucrose fatty acid polyester heated to 200° C., 20% citric acid aqueous solution was added in the amount of 0.05% by weight. The resulting mixture was agitated and then cooled to room temperature to obtain a desired stabilized sucrose fatty acid polyester.

TEST EXAMPLE 2

As to each of the stabilized sucrose fatty acid polyesters obtained in Examples 2 and 3 (Test Samples B and C) and non-treated sucrose fatty acid polyester (Control Sample), the AOM test carried out, as in Test Example 1, to check a stability thereof to oxidation.

Results are shown in following Table 2, from which it is apparent that the treatment according to the invention provides a remarkable increase in stability of the polyol fatty acid polyester.

TABLE 2

| Sample | Peroxide Value (meq./kg) | | |
|---|---|---|---|
| | After 6 hr. | After 10 hr. | After 14 hr. |
| Test B | 8.9 | 12.3 | 20.6 |
| C | 11.5 | 15.5 | 29.3 |
| Control | 24.9 | 37.2 | 137 |

EXAMPLE 4

The sucrose fatty acid polyester was mixed with a commercially available refined soybean oil in a weight ratio of 1:1, and the resulting mixture was treated as in Example 1 to obtain a desired mixture of the stabilized sucrose fatty acid polyester and the soybean oil.

TEST EXAMPLE 3

As to each of the mixture obtained in Example 4 (Test Sample D) and a mixture of untreated sucrose fatty acid polyester and the refined soybean oil (weight ratio of 1:1, Control Sample), a dish-oven test was carried out to check a stability thereof to oxidation.

The test was carried out as follows. Each of the samples was heated to cause a melt thereof. The melted sample was charged in a glass-dish (diameter; 50 mm, depth; 13 mm) by 2 g and the dish was put in a thermostat kept at 55° C. Under such conditions, a peroxide value of the sample, increasing with time was measured from time to time.

Results are shown in following Table 3, from which it is apparent that the treatment according to the invention provides a remarkable increase in stability of the polyol fatty acid polyester.

TABLE 3

| Sample | Peroxide Value (meq./kg) | | |
|---|---|---|---|
| | After 6 hr. | After 10 hr. | After 14 hr. |
| Test D | 6.2 | 8.5 | 19.8 |
| Control | 16.4 | 37.1 | 280 |

EXAMPLE 5

To sucrose fatty acid polyester heated to about 60° C. to cause a melt thereof, malic acid in the form of powder was added in 0.01% by weight and the resulting mixture was sufficiently agitated.

Then, the malic acid was recovered through a filtration to obtain a desired stabilized sucrose fatty acid polyester.

EXAMPLE 6

The procedure described in Example 5 was repeated except that tartaric acid was employed in same amount, in place of the malic acid, to obtain a desired stabilized sucrose fatty acid polyester.

REFERENCE EXAMPLES 1 TO 5

The procedure described in Example 5 was repeated except that one of the following basic acids was employed in same amount, in place of the malic acid to obtain a treated sucrose fatty acid polyester.

(a) Stearic acid (as an exemplar for monobasic acids),
(b) Maleic acid (as an exemplar for dibasic acid),
(c) Phthalic acid (as an exemplar for dibasic acids),
(d) Lactic acid (as an exemplar for monobasic oxy acids), and
(e) Salicylic acid (as an exemplar for monobasic oxy acids)

TEST EXAMPLE 4

As to each of the treated sucrose fatty acid polyesters obtained by Examples 5 and 6 (Test Samples E and F), Reference Examples 1 to 5 (Reference Samples a to e), and non-treated sucrose fatty acid polyester (Control Sample), an AOM (Active Oxygen Method) test was carried out, in the manner described in Test Example 1, to check a stability thereof to oxidation.

Results are shown in following Table 4, from which it is apparent that the treatment according to the invention using a polybasic oxy acid provides a desired stabilization for the polyol fatty acid polyester, but no desired effect can not be attained by the treatment using other basic acids such as monobasic acids, monobasic oxy acids and polybasic acids.

TABLE 4

| Sample | Peroxide (meq./kg) | | |
|---|---|---|---|
| | After 6 hr. | After 10 hr. | After 14 hr. |
| Test E | 10.5 | 15.5 | 28.0 |
| F | 10.3 | 16.9 | 33.0 |
| Reference a | 25.3 | 40.2 | 126 |
| b | 30.1 | 77.8 | 208 |
| c | 52.9 | 189 | — |
| d | 20.0 | 65.3 | 119 |
| e | 42.5 | 99.1 | 195 |
| Control | 24.9 | 37.2 | 137 |

What is claimed is:

1. A process for stabilizing an esterified polyol fatty acid polyester against oxidation comprising the steps of:
    (a) contacting a polyol fatty acid polyester esterified to an extent of at least 40% with a polybasic oxy acid at a temperature above the melting point of the polyol fatty acid polyester; and
    (b) separating the polyol fatty acid polyester from the polybasic oxy acid to obtain a polyol fatty acid polyester stabilized against oxidation.

2. A process as claimed in claim 1, wherein the polyol of said polyol fatty acid polyester to be esterified is selected from the group consisting of erythritol, xylitol, sorbitol, glucose and sucrose.

3. A process as claimed in claim 1, wherein the fatty acid of said polyol fatty acid polyester to be esterified is selected from the group consisting of caprylic acid, capric acid, lauric acid, myristic acid, myristoleic acid, palmitic acid, palmitoleic acid, stearic acid, oleic acid, elaidic acid, ricinoleic acid, linoleic acid, linolenic acid, eleostearic acid, arachinic acid, arachidic acid, behenic acid, erucic acid, docosahexaenic acid, eicosapentaenic acid and a mixture thereof.

4. A process as claimed in claim 1, wherein the polybasic oxy acid used as a stabilizer is selected from the group consisting of citric acid, malic acid and tartaric acid.

5. The process according to claim 1, wherein the polybasic oxy acid is in a solid state when first contacted with the polyol fatty acid polyester.

6. The process according to claim 1 wherein the polybasic oxy acid is separated from the polyol fatty acid polyester by filtration.

7. The process according to claim 1, wherein the polyol fatty acid polyester and polybasic oxy acid are contacted by passing the polyol fatty acid polyester through a filtration bed or layer containing the polybasic oxy acid.

* * * * *